United States Patent [19]

Brennan

[11] Patent Number: 5,169,380
[45] Date of Patent: Dec. 8, 1992

[54] TREATMENT OF SLEEP DISORDERS AND ALLEVIATING DISRUPTION OF CIRCADIAN RHYTHMS

[76] Inventor: Michael J. W. Brennan, Centralbahnstrasse 9, Switzerland

[21] Appl. No.: 664,504

[22] Filed: Mar. 5, 1991

Related U.S. Application Data

[63] Continuation of Ser. No. 346,787, May 3, 1989, abandoned.

[30] Foreign Application Priority Data

May 4, 1988 [ZA] South Africa .................. 88/3166

[51] Int. Cl.$^5$ .................................. A61M 21/00
[52] U.S. Cl. ......................... 600/26; 600/14; 128/639; 128/644; 128/421; 128/791
[58] Field of Search .............. 600/26, 13, 14; 128/639, 644, 419 R, 421, 422, 783, 791, 799, 380, 802

[56] References Cited

U.S. PATENT DOCUMENTS

| | | | |
|---|---|---|---|
| 3,464,416 | 9/1969 | Williams | 600/26 |
| 3,658,051 | 4/1972 | MacLean | 600/14 |
| 3,669,119 | 6/1972 | Symmes | 600/26 |
| 3,762,396 | 10/1973 | Ballentine et al. | 128/791 |
| 3,841,305 | 10/1974 | Hallgren | 128/419 R |
| 3,841,306 | 10/1974 | Hallgren | 128/419 R |
| 3,881,495 | 5/1975 | Pannozzo et al. | 128/442 |
| 4,197,881 | 4/1980 | Fellus | 128/422 |
| 4,266,532 | 5/1981 | Ryaby et al. | 128/421 |
| 4,412,840 | 11/1983 | Bentall | 128/422 |
| 4,503,863 | 3/1985 | Katims | 600/26 |
| 4,641,633 | 2/1987 | Delgado | 600/13 |
| 4,723,536 | 2/1988 | Rauscher et al. | 600/14 |
| 4,770,180 | 9/1988 | Schmidt et al. | 128/644 |
| 4,809,700 | 3/1989 | Castelli | 128/644 |
| 4,889,526 | 12/1989 | Rauscher et al. | 600/14 |

FOREIGN PATENT DOCUMENTS

3612984 11/1986 Fed. Rep. of Germany ........ 600/26

*Primary Examiner*—Randall L. Green
*Assistant Examiner*—K. Reichle
*Attorney, Agent, or Firm*—Nikaido, Marmelstein, Murray & Oram

[57] ABSTRACT

Apparatus for alleviating disruptions in the circadian rhythms of a mammal comprises a pair of electrodes 11 mountable on either side of the head 12. The apparatus further comprises a voltage generator for generating a voltage alternating at a rate of between 5 and 40 cycles per second with a peak to peak voltage value of at least 100V. The electrodes being connected to the generator so that an alternating electric field is generated between them. In a method of alleviating circadian disruptions in a mammal, the mammal's brain region is subjected to the aforementioned alternating electric field.

10 Claims, 5 Drawing Sheets

TREATMENT OF SLEEP DISORDERS AND ALLEVIATING DISRUPTION OF CIRCADIAN RHYTHMS

This application is a continuation of application Ser. No. 346,787 filed May 3, 1989, now abandoned.

This invention relates, inter alia, to a method of altering or varying various neuro-physiological mechanisms, which mechanisms control the timing of various rhythms in the human body such as the human sleep-wake, body core temperature, metabolic and endocrine rhythms. The invention also relates to apparatus for carrying out the method.

BACKGROUND OF THE INVENTION

Virtually all human biological functions show rhythms which vary predictably over a period of just more than 24 hours. Control of these rhythms and their synchronisation to the normal 24-hour day depend on a specific brain region, which hence may be regarded as the body's clock.

The proper functioning of the clock enables the internal sleep-wake, core temperature and other rhythms of man to synchronise with the changing demands of the external environment and thereby to ensure optimal performance.

The period of most of these rhythms approximates, but does not equal, 24 hours and this is the meaning the applicant attaches to the term 'circadian rhythms'. The biological clock must therefore be re-set every 24 hours. This phase shift to re-set the biological clock hence enables the human to adapt to changing schedules. This re-set capability is, however, subject to certain very specific constraints. Features of our modern life, like electric lighting, jet-travel across time zones and round-the-clock work schedules have imposed conditions on the human circadian timing system which stress the biological clock beyond its capacity to maintain synchronisation of the body's rhythms with the external environment.

It is known that the hypothalamus, situated at the base of the brain, contains the nerve centres responsible for the timing of circadian rhythms. It is also known that neurotransmitters, which are chemicals contained in the nerve endings of nerve cells in the brain, and by means of which the cells communicate with each other, are released by the influx of calcium ions into the nerve endings.

One of these transmitters, the inhibitory transmitter γ-ammobutyric acid (GABA), which is present in a large number of nerve cells (neurons) in the central nervous system and in the hypothalamus, is known to have a large part to play in the control of human circadian rhythms.

Recently scientists have appreciated that ability to learn new information, concentration and vigilance, motor co-ordination, appetite, mood and even sexual functions is profoundly affected by disruptions of the circadian timing system. A recent US Congressional report suggest that psycho-social and physical problems resulting from circadian rhythm disruption may represent one of the major public health issues of the century.

It is an object of this invention to provide a method which it is believed will alleviate disruptions in a mammal's circadian rhythms and also to provide apparatus for carrying out the method.

SUMMARY OF THE INVENTION

According to the invention there is provided apparatus for modifying the activity of neuro-transmitters in a mammal's brain region comprising:
a generator for generating a changing voltage causing a changing electric field;
the voltage changing at a rate of between 5 and 40 cycles per second with a peak to peak value of at least 100 V; and
a pair of electrodes connectable to the generator and mountable adjacent the mammal's head on either side thereof for subjecting at least part of the mammal's brain region to the changing electric field generated between the electrodes.

The words "brain region" will be used in this specification to denote the brain and the hypothalamus. By subjecting at least part of the brain region to the alternating electric field, it is believed that an influx of calcium ions ($Ca^{2+}$) into the nerve endings is facilitated, which in turn regulates and facilitates the release of neurotransmitters. Recent experiments have shown that, in particular, the release of GABA is increased when neural tissue is exposed to an alternating electric field.

Tests have also shown that the apparatus according to the invention alleviates disruptions in circadian rhythms and hence assists the biological clock in re-setting itself.

The voltage preferably is an alternating voltage having a frequency of substantially 10 cycles per second and a peak to peak voltage value of substantially 600 V. The voltage may change according to any suitable wave form such as a sinusoidal wave.

However, in the most preferred embodiment the voltage changes in the form of a square wave between ground potential and substantially 600 V and has a duty cycle of 50%.

A carrier may be provided for mounting the electrodes on either side of the mammal's head.

In the preferred embodiment each electrode comprises a copper disc on a base layer of a dielectric material and a second layer of a dielectric material covering the copper disc, the copper disc being connectable to the generator.

In this embodiment the carrier comprises a head band and each electrode comprises a hook-shaped clip on the base layer for mounting the electrode on the head band. The head band is preferably made of a resiliently stretchable fabric and the electrodes are preferably circular with a diameter of 11 cm.

In another embodiment each electrode comprises a conductor embedded in a dielectric material, the conductor being formed in a spiral and the dielectric material being PERSPEX(methyl methacrylate resin), the carrier comprising a U-shaped head band adapted to fit over the mammal's head to hold the electrodes on either side of the mammal's head.

In a further embodiment of the invention, the required electrodes may be arranged in spaced relationship in a form of a cap or dome which is locatable over the subject's head. Such a device could have the appearance of a conventional hair dryer.

In another embodiment a bed may be equipped with mountings for the electrodes which, preferably, allow for adjustments of the spacing of the electrodes.

In yet a further embodiment of the invention, the electrodes may be mounted on appropriate walls of a room in which a patient is to be treated.

According to another aspect of the invention a method of modifying the activity of neurotransmitters in a mammal's brain region comprises the steps of:

generating a changing electric field by generating a voltage changing at a rate of between 5 and 40 cycles per second with a peak to peak voltage value of at least 100 V; and subjecting the mammal's brain region to the changing electric field by mounting a pair of electrodes connected to the generator adjacent the head, on either side thereof.

The method may be intended to cause or facilitate the release of neurotransmitters.

The method may also be intended to modify the activity of neurotransmitters on a post synoptic membrane in the mammal's brain region.

The method may further be intended to alleviate disruptions in at least some of the mammal's circadian rhythms.

According to the invention there is also provided a method of alleviating sleep disorders in a mammal comprising the steps of:

generating a changing electric field by generating an alternating voltage changing in the form of a square wave at a rate of between 5 and 40 cycles per second with a substantially 50% duty cycle and between ground potential, and substantially 600 V; and applying the field across the mammal's head so that at least the hypothalamus is subjected to the field.

Applicant has found that a frequency of substantially 10 cycles per second yields the best results and that a field strength of at least 590 V/m in free air, corresponding to a voltage of substantially 100 V, is required to provide satisfactory results. The field strength E is arrived at by dividing the applied voltage of 100 V by 0.17, the distance between the sides of the average human head.

It is believed that the release of GABA is effective in treating insomnia, anxiety states and circadian disruptions such as jet lag and that suffered by shift workers. It is further believed that the method according to the invention may be useful in treating depression, obesity, hyperphagic syndromes, hypertension and conditions where cardiac after-load is important, such as congestive heart failure. The method may also be effective as a muscle relaxant.

The method may also affect processes mediated by other neurotransmitters such as the cathecholamines, acetycholine, serotonin, other amino acids such as glycine, taurine, glutamate, aspartate and the whole family of neuropeptides. It is possible that the effects of the alternating electric field may be mediated through alterations in post-synoptic receptor sensitivities to the abovementioned transmitters.

Circadian Timing Systems

It is believed that disruptions in the circadium timing system, more specifically the sleep-wake cycle and body core temperature cycle, are the underlying cause of various sleep disturbances such as the condition of so-called "nonspecific insomnia".

It is known that the sleep-wake and body core temperature cycles are endogenously generated to have free-running periods, that is without the influence of environmental time cues, of just greater than 24 hours, averaging 25 to 27 hours.

It is the function of the body's biological clock to entrain these rhythms to the normal 24 hour day. Various independent researches have identified a small bilateral pair of nuclei in the anterior hypothalamus, the suprachiasmatic nuclei (SCN), as a circadian pacemaker. Since the circadian system, which runs with a period greater than 24 hours under isolation conditions, is entrained to a 24 hour period in natural environments, it is apparent that circadian systems are sensitive to some environmental time cues. Were this not so, we would fall asleep sequentially later each day, moving progressively out of phase with the environmental day-night cycles. The light-dark cycle is one important time cue in all mammalian species including man. Other relevant time cues are regularly timed meals, environmental temperature cycles, social cues and fluctuations in ambient noise levels.

Entrainment of Circadian Rhythms by Environmental Time Cues

In a series of experiments designed to investigate the effect of environmental time cues, subjects were studied in isolation units constructed to eliminate all environmental cues. A reference experiment was simultaneously performed in an unshielded unit.

It was found that in the unshielded unit, the circadian periods were significantly shorter than in the shielded unit. Thus, naturally present cues reduced the period of free-running sleep-wake and temperature rhythms towards 24 hours. On the other hand, there was a great tendency towards internal desynchronisation in subjects studied in the shielded unit. By internal desynchronisation is meant that the sleep-wake rhythm ran with a period significantly different from that of the core temperature rhythm in the same subject. The shielding of the circadian system from environmental cues had allowed uncoupling of the sleep-wake and body core rhythms. During these periods of internal desynchronisation, subjects complained of inability to fall asleep when they wished to do so and of feelings of anxiety and tension and even depression. All subjects who developed internal desynchronisation reported lying in bed for long periods before being able to go to sleep, and many also reported disturbed sleep with frequent awakenings. No such complaints were voiced by subjects in the unshielded unit.

In a significant number of subjects, the period of sleep-wake and temperature cycles was shorter during artificial field application than without it and by an average of 1.3±0.7 hours. Moreover, the shortening effect of the field was greater for those subjects with the longest circadian cycles in the absence of the field; this resulted in larger interindividual differences during the test sections without field than when the field was in operation.

The effect of the artificial field on internal desynchronisation was evident in two ways. In some subjects who had been exposed to the field from the start of the experiment, internal desynchronisation occurred when the field was switched off. Complaints of insomnia and feelings of anxiety attended the desynchronisation.

In other experiments, spontaneously present internal desynchronisation ceased immediately when the artificial field was switched on.

A significant number of subjects experienced internal desynchronisation when they were protected from all fields, but not one case of internal desynchronisation occurred while the artificial field was in operation.

A set of control experiments was performed in which DC electric fields (600 V/m) were applied in the shielded unit. These steady fields did not shorten the periods of free-running circadian rhythms, nor did they influence any other parameter of the rhythm or affect internal desynchronisation.

Additional preliminary data suggest that brief exposure to the field (1 hour) at 24 hour intervals is sufficient to entrain sleep-wake and temperature rhythms, and to prevent internal desynchronisation. Thus entrainment would seem to be based on a single response to the field, with that response having a decay time of the order of one day.

Mechanism of Action of Electric Fields

The demonstration that sleep-wake and temperature rhythms can free-run with different periods in the same individual, suggests that more than one pacemaker is involved in circadian rhythm generation. Under normal conditions there is a coupling between the suprachiasmatic nuclei SCN, identified as a major pacemaker, and other putative and as yet unidentified pacemakers. Present data suggest that the SCN regulates one group of rhythmic functions, including sleep-wake cycles, while other rhythms, notably core body temperature are independently regulated. Since internal desynchronisation involves a shortening or lengthening of the sleep-wake period while the temperature period remains relatively stable, it seems that the effect of electric fields is mediated through the SCN. The applicant hypothesizes that as the period of SCN-generated rhythms moves outside a critical range, by becoming too short or too long, coupling between the SCN pacemaker and the core temperature pacemaker breaks down. The action of electric fields is thus to prevent SCN-generated rhythm periods moving outside the range of coupling imposed by the nature of the core temperature pacemakers.

As long as the sleep-wake and core temperature rhythms remain coupled, the subject has no trouble in sleeping at the appropriate times. When desynchronisation occurs sleep-onset latencies are prolonged.

There are now many data which demonstrate unequivocally that sleep-onset latency and duration of sleep in normal human beings is determined by the phase of the core temperature rhythm, rather than the length of the period of prior wakefulness. Thus, the propensity for sleep is greatest when the body temperature is in a falling phase. Also, the internal structure of the sleep episodes varies with the phase of the temperature cycle at the onset of sleep. This is true regardless of how long subjects have been awake prior to trying to go to sleep. In subjects in whom core temperature and SCN-generated rhythms are uncoupled, sleep is difficult because the phase of the temperature cycle is not conducive to sleep at the same time as the SCN is signalling that sleep would be appropriate.

The precise neurochemical mechanisms underlying period changes in SCN-dependent rhythms are not yet clearly understood. Several lines of evidence suggest that the inhibitory neurotransmitter gamma-aminobutyric acid (GABA) plays an important role. High levels of GABA and its synthetic enzyme glutamate decarboxylase (GAD) are present in the hypothalamus of rats, monkeys and man. The levels of GAD in the small interneurons of the SCN are the highest in the hypothalamus.

The applicant has demonstrated that administration of sodium valproate, a drug which enhances GABA-mediated inhibition, to free-running squirrel monkeys is capable of either shortening or lengthening the periods of activity rhythms.

Corroboratory evidence was obtained from 24-hour recordings of multiple unit activity in slices of rat SCN. These preparations demonstrate cyclical activity in vitro. Application of GABA to the slices produced inhibition of spontaneous neuronal firing in a manner that was markedly phase-dependent.

It therefore seems clear that the small GABA-ergic interneurons intrinsic to the SCN are major elements in the generation of circadian rhythms.

Low frequency electric fields have been reported to have a wide variety of effects in many biological tissues. The basic mechanism of these actions is a facilitation of $Ca^{2+}$ and, possibly, hydrogen ion fluxes across cell membranes. This is of great significance in nervous tissue, since release of neurotransmitters from nerve endings is strictly $Ca^{2+}$-dependent.

The applicant has examined the effects of low frequency electric fields on the release of $^3$H-GABA from preloaded synaptosomes prepared from rat brain. At 10 Hz, 600 V/m (in air) the spontaneous efflux of $^3$H-GABA was increased by 16±4% over baseline, while $K^+$(15 mM)-depolarisation-induced release was enchanced by 48±12%. The experimental system minimises metabolism of the $^3$H-GABA and essentially eliminates re-uptake of released transmitter, consequently the effect of the electric field was on GABA release rather than an inhibition of re-uptake. Frequencies of 1 Hz and 45 Hz were found not to have a significant effect on transmitter efflux or depolarisation-induced release.

BRIEF DESCRIPTION OF THE DRAWINGS

The invention will now further be described, by way of example only, with reference to the accompanying diagrams wherein.

DESCRIPTION OF PREFERRED EMBODIMENT

Figure 1:
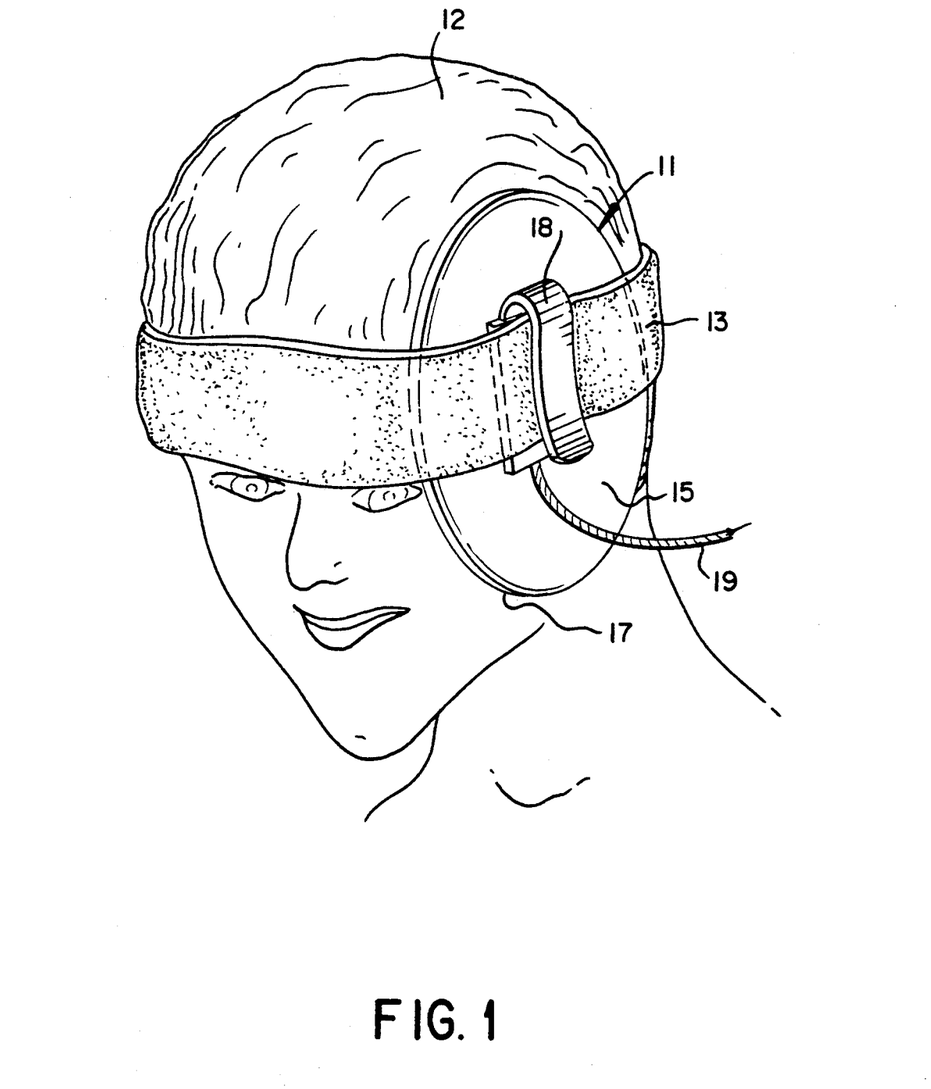
FIG. 1: is a perspective view of a human head and showing one of two electrodes forming part of the apparatus according to the invention mounted on one side thereof.

In FIG. 1 there is shown part of the apparatus for modifying the activity of neurotransmitters in a mammal's brain region. The apparatus comprises a pair of electrodes 11, mountable on either side of the human's head 12. In the figure only one electrode 11 is shown, but another similar electrode is mounted on the other side of the head.

A carrier in the form of a resiliently stretchable head band 13 is provided to hold the electrodes 11 in position on either side of head 12. The head band is in the form of a closed loop and is made of a resiliently stretchable fabric.

Figure 2:
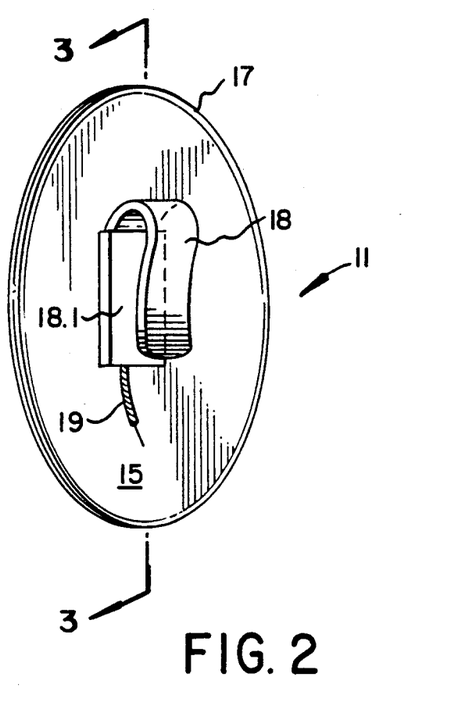
FIG. 2: is a perspective view of the electrode itself.
Figure 3:
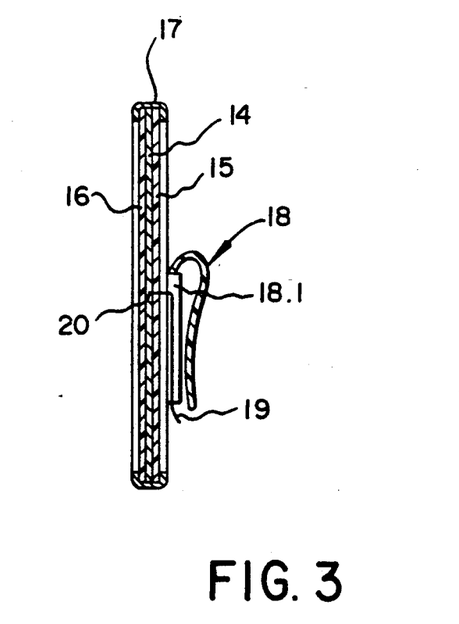
FIG. 3: is a section on line III of the electrode in FIG. 2.

Referring now to FIGS. 2 and 3 the electrode comprises a copper disc 14 on a base layer 15 of a suitable dielectric material, such as that offered for sale under the trade name MYLAR (polyethylene terephthalate). The other face of disc 14 is covered with a layer 16 of a plastic material. In use, the layer 16 faces the head 13 of the person to be treated. A circular, channel shaped rim 17 is provided to cover the peripheral region of the electrode.

A U-shaped clip 18 is mounted on the outside face of base layer 15. In use, the electrode is mounted on band 12 with the clip straddling the band as shown in FIG. 1.

An insulated electric wire 19 is connected to copper disc 14 at 20 and passes through leg 18.1 mounted on base layer 15. In use, the wires 19 of the two electrodes are connected to an output of a voltage generator to be described herebelow.

Figure 4:
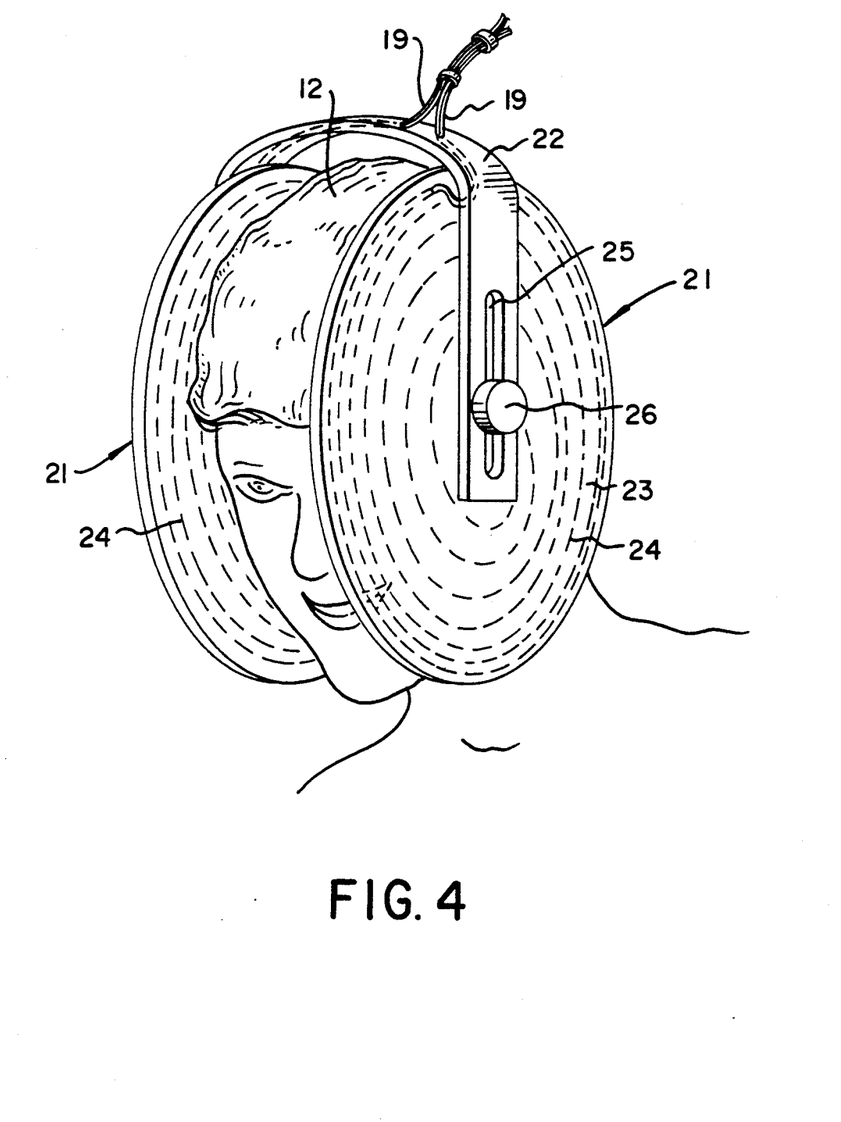
FIG. 4: is a diagrammatic perspective view of another embodiment of the electrodes of the apparatus according to the invention mounted on a human's head.

In FIG. 4 there is shown another embodiment of the electrodes for the apparatus according to the invention. These electrodes, designated by the reference numeral 21, are mounted on the head 12 by a U-shaped band 22 adapted to pass over the head to hold the electrodes on either side of the head. Each of the identical electrodes comprises a PERSPEX (methyl methacrylate resin) disc-like body 23 in which an electric conductor, arranged in the form of a spiral 24 is embedded. In other embodiments the conductor may be arranged in the form of a mesh (not shown).

Electrodes 21 are mounted to be adjustable on the band 22 to permit them to be manipulated thereon so that the centre of an electric field generated between the electrodes extends through the hypothalmus, an area situated at the base of the brain and which is involved in the timing of circadian rhythms.

The means for permitting the adjustability of the electrodes on the band comprises a slot 25 defined in band 22 and a threaded peg (not shown) mounted on perspex body 23. The peg is slidable in the slot and when a desired position is reached, the electrode is fastened on band 22 by means of nut 26.

Insulated electric conductors 19 are provided for connecting the aforesaid conductor arrangement 24 to a voltage generator to be described herebelow.

Figure 5:
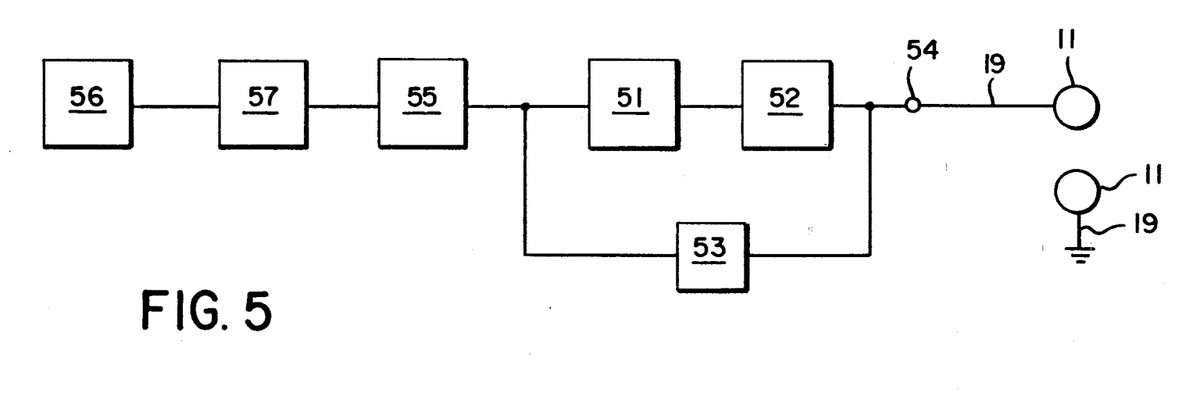
FIG. 5: is a block diagram of the electronic circuitry of a voltage generator forming part of the apparatus according to the invention.

In FIG. 5 there is shown a block diagram of a voltage generator 50 making up the rest of the apparatus according to the invention. The generator 50 is connectable to the electrodes 11 described hereabove with reference to FIGS. 1 to 3 via electric wires 19 to generate an alternating electric field between the electrodes.

The generator 50 comprises an oscillator stage 51 connected to a voltage multiplier stage 52. A voltage regulator 53 is connected in a feed-back loop between the output of the generator at 54 and the oscillator stage 51.

A timer 55 for controlling the operation of the oscillator 51 is connected to oscillator 51. This timer is programmable to start the oscillator 51 for a programmed length of time starting at a programmed point in time. After the aforesaid length of time the oscillator is switched off again.

A power supply comprising a plurality of batteries (not shown) is designated by the reference numeral 56. The batteries may be rechargeable or non-rechargeable. A low voltage warning circuit 57 is connected to the power supply 56 and comprises a lamp (not shown) to indicate when the voltage of the batteries has become too low. In certain embodiments a power supply (not shown) connectable to mains may also be provided.

Figure 6:
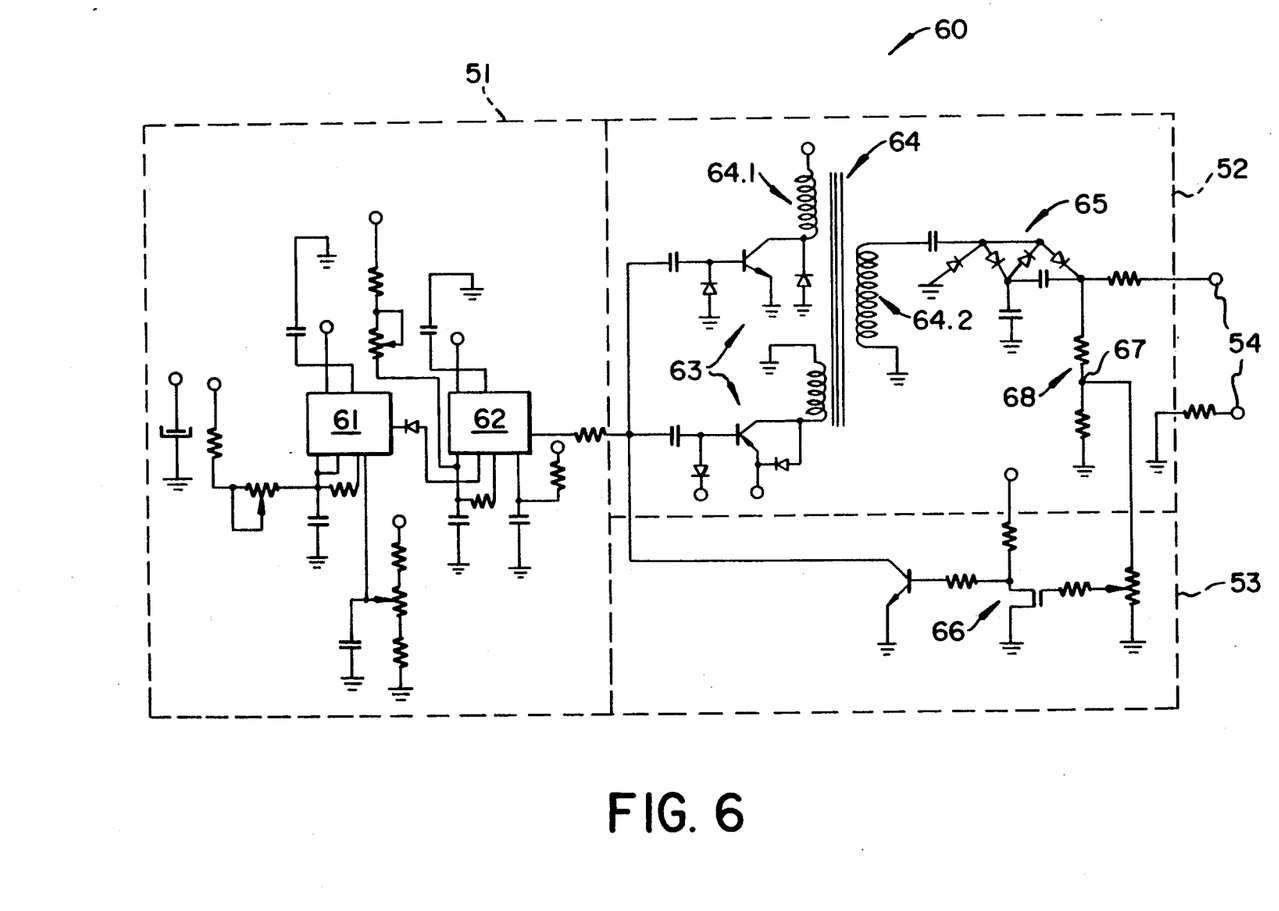
FIG. 6: is a circuit diagram of part of the voltage generator.

In FIG. 6 there is shown a circuit diagram 60 of oscillator stage 51, voltage multiplier stage 52 and voltage regulator stage 53 of the block diagram in FIG. 5.

Oscillator stage 51 comprises two 555 timers 61 and 62 and is designed to generate an alternating voltage changing in the form of a square wave. The duty cycle of the alternating voltage is 50%. The output of the oscillator is connected via a driver stage 63 to the primary winding 64.1 of a step-up transformer 64. The secondary winding 64.2 of transformer 64 is connected to a voltage tripler 65. The output of tripler 65 is connected to the output 54 of the voltage generator.

Voltage regulator 53, comprising a junction field effect transistor 66 to minimise current consumption, is connected between point 67 in voltage divider network 68 and the input to the driver stage 63 for the primary winding of the step-up transformer 64.

The voltage generated at the output 54 of the generator alternates in the form of a square wave at a frequency of 10 cycles per second and between 600 V and ground potential. The duty cycle of the changing voltage is 50 percent.

As shown in FIG. 5, in use, wire 19 of one electrode is connected to the ground potential terminal of the generator output 54 and the wire 19 of the other electrode is connected to the other terminal of the generator output 54. It will be appreciated that with the electrodes 11 so connected, an alternating electric field is generated between electrodes 11. The field so generated, before application to the head and in free air, alternates in the form of a square wave at a rate of 10 cycles per second and between zero and 3530 V/m in free air. The field strength is calculated using the formula $E = v/d$ where E is the field strength in Volts per meter, V is the applied voltage and $d = 0,17$ m, the distance between the electrodes i.e. the distance between the sides of the average human head.

In some embodiments the voltage generator 15 may be provided with additional output terminals to permit suitable electronic instruments to be connected thereto so that the user may be in a position continuously to monitor the wave form, voltage and the frequency of the output signal.

Clinical Trials

A series of tests to be described herebelow were conducted with the apparatus described hereabove with reference to FIGS. 1 to 3, 4 and 5.

Three main groups of subjects participated: I prolonged sleep-onset latency (trouble falling asleep); II middle insomnia (trouble maintaining sleep), and III unsatisfying sleep, but without specific difficulty in any sleep parameter. Candidates were interviewed by a sleep specialist who evaluated their sleep problems and excluded those for whom specific diagnosis could be made. Current use of hyprotics was not considered a reason for exclusion.

The protocol was as follows. Subjects were asked to complete a standardised sleep log as soon as possbile after waking in the morning. Data recorded referred to that night's sleep just ended, and comprised: time of lights out, estimated sleep latency in minutes, recalled awakenings after falling asleep, estimation of total time awake during the night, time of final awakening and total sleep time. Subjects also recorded hypnotic use (type, dose and time of taking), as well as details of alcohol use after 17h00. They were asked to record any unusual features of their sleep and the occurrence of any unusual events during the night. During the day, subjects completed a fatigue rating scale at 10h00, 14h00 and 18h00. The scale ranged from 1 (active and vital; wide awake) to 8 (asleep; napping) and was derived from the Stanford Sleepiness Scale prepared by the Stanford University Medical Center's Sleep Disorders Center.

Baseline data were gathered over a first period of 14 to 21 days, following which subjects were allocated at random either a functioning device (active) or a placebo device in which an internal switch rendered the device inoperative. Subjects were instructed to use the device for, in the first instance, the hour immediately before switching off lights at bedtime. They were given a free choice as to where to use the device. In general subjects used the devices in bed or in an easy chair while reading, watching television or listening to music.

Subjects continued to record sleep data while using the devices each night. After a second period of between 16 and 22 days, the devices were returned and those who had received placebo devices were given active devices and asked to continue keeping records. It was difficult to introduce a placebo phase to those subjects who had used active devices initially, since many of them continued to fall asleep quickly and to sleep well when the active devices were withdrawn. Those who relapsed when use of active devices were discontinued, were given placebo devices.

After a third recording period of between 18 and 24 days, all those who wished to continue using devices were switched to active devices and asked to keep nightly sleep records for as long as they continued their use.

I Prolonged Sleep-Onset Latency

A total of 40 subject participated: 10 male with ages between 19-26 years (mean 37.2) and 30 female with ages between 14 and 67 years (mean 43.7). Duration of insomnia was 4 months-25 years (average 6 years). 19 Subjects were using hypnotics at the time of the tiral. The results are presented in table 1 in four groups.

TABLE 1

|  |  | Sleep-onset latency (mins) |
| --- | --- | --- |
| OVERALL | Baseline | 77.6 ± 9.3 |
| 10 male | Active | 29.2 ± 4.0* |
| 30 female |  |  |
| PLACEBO PHASE | Baseline | 80.0 ± 12.6 |
| FIRST | Placebo | 59.7 ± 14.8 |
| 5 male | Active | 24.0 ± 5.3* |
| 14 female |  |  |
| ACTIVE FOLLOWED | Baseline | 98.5 ± 9.9 |
| BY PLACEBO | Active | 36.6 ± 4.8** |
| 3 male, | Placebo | 101.0 ± 17.1 |
| 5 female |  |  |
| ACTIVE WITH | Baseline | 74.2 ± 6.9 |
| NO PLACEBO | Active | 28.9 ± 3.6* |
| 2 male |  |  |
| 11 female |  |  |

*Significantly different from baseline/placebo $p < 0.001$
**Significantly different from baseline/placebo $p < 0.005$.

II Middle Insomnia

Fifteen subjects participated: 6 male with ages between 30 and 62 years (mean 43) and 9 female with ages between 36-67 years (mean 49). Duration the problem was 12 months-20 years (average 8 years); 11 subjects were using hypnotics. The results are reflected in Table 2.

TABLE 2

|  | Recalled awakenings per night | Estimated time awake per night (min) |
| --- | --- | --- |
| Baseline or Placebo | 2.6 ± 0.41 | 113 ± 19.3 |
| Active | 1.2 ± 0.27 | 48 ± 11.8* |

*Significant difference form baseline/placebo $p < 0.01$

II Unsatisfying Sleep

Four subjects participated, 3 male with ages between 19 and 52 and 1 female of 39 years of age. Subjects complained that they did not feel rested after sleep, although they did not complain of trouble falling asleep.

Although the number of subjects is too small to be statistically valid, all subjects reported improvement in sleep quality while using active devices.

Although the results presented in Tables 1 and 2 are the subjective assessments of participants in the trials, there is a clear-cut reduction in sleep-onset latency during active device phases as compared with baseline or placebo phases. An overall improvement of 62% was documented, bringing average sleep-onset latency into the range of normal subjects (10±9 min).

Also, nocturnal awakenings and time awake at night were reduced although not as significantly as was sleep-onset latency.

These data have been confirmed in sleep laboratory studies. A brief summary of the major sleep laboratory findings is shown in Table 3.

TABLE 3

| Major effects of active vs placebo device in polysomnographic studies | |
| --- | --- |
| Sleep-onset latency | 57% reduction |
| Total sleep time | 4% increase |
| Time awake at night | 71% reduction |
| REM sleep | 15% reduction |
| Total cumulative shifts between stages | 25% reduction |

In summary, the use of the apparatus according to the invention has been shown to be effective in treating insomnia, especially that characterized by a prolonged sleep-onset latency. Indeed, sleep improved with continued use of active device, unlike the continued use of hypnotics which produces tolerance. No side-effects have been observed after 14 months of continuous use.

I claim:

1. An apparatus for alleviating disruptions in circadian rhythms in a mammal comprising:
 a pair of electrodes wherein each electrode comprises
 (1) a substantially planar conducting member and
 (2) a layer of dielectric material;
 head band means, removably connected to said electrodes, for electrically insulating the electrodes from one another while mounting said electrodes adjacent substantially opposite external regions of the head of the mammal, respectively, with the layer of dielectric material positioned between the head and the conducting member and at least part of the mammal's brain region located between the pair of electrodes; and
 generator means, removably connected to the conducting members, for generating an electric voltage changing at a rate between 5 and 40 cycles per second with a peak to peak value of at least 100 V so as to create a changing electric field between the conducting members to alleviate disruptions in circadian rhythms.

2. An apparatus as claimed in claim 1 wherein the head band means is annular and is made of a resiliently flexible material.

3. An apparatus as claimed in claim 1 wherein each electrode further comprises a base layer of a dielectric material, and wherein the conducting member in each electrode comprises a copper disc sandwiched between said layer of dielectric material and said base layer.

4. An apparatus as claimed in claim 3 wherein each electrode further comprises a U-shaped clip on the base layer mounting the electrode on the head band means.

5. An apparatus as claimed in claim 1 wherein said conducting member comprises an elongate member wound in a substantially planar spiral, said layer of dielectric material is a layer of methyl methacrylate resin wherein said spiral is embedded, and said head band means is substantially U-shaped.

6. An apparatus as claimed in claim 1 wherein said conducting member is circular with a diameter of substantially 11 cm.

7. A method of alleviating disruptions in circadian rhythms in a mammal comprising the steps of:
mounting a pair of electrodes connected to a generator adjacent substantially opposite external regions of the head of said mammal, respectively, with at least part of the mammal's brain region located therebetween, and;
generating with the generator an electric voltage changing at a rate of between 5 and 40 cycles per second with a peak to peak voltage value of at least 100 V so as to create a changing electric field between the electrodes and subjecting the mammal's brain region thereto.

8. A method as claimed in claim 7 wherein the generating step further includes generating said voltage in the form of a square wave with a duty cycle of substantially 50% and a frequency of substantially 10 Hz.

9. An apparatus for alleviating sleep disorders in a mammal comprising:
a pair of electrodes wherein each electrode comprises (1) a substantially planar conducting member and (2) a layer of dielectric material;
head band means, removably connected to said electrodes for electrically insulating the electrodes from one another while mounting said electrodes adjacent substantially opposite external regions of the head of the mammal, respectively, with the layer of dielectric material positioned between the head and the conducting member and at least part of the mammal's brain region located between the pair of electrodes; and
generator means, removably connected to the conducting members, for generating an electric field changing at a rate between 5 and 40 cycles per second with a peak to peak value of at least 590 V/m in free air between the conducting members to alleviate sleep disorders.

10. A method for alleviating sleep disorders in a mammal comprising the steps of:
mounting a pair of electrodes connected to a generator adjacent substantially opposite external regions of the head of said mammal, respectively, with at least part of the mammal's brain region located therebetween, and;
generating with the generator an electric field changing at a rate of between 5 and 40 cycles per second with a peak to peak value of at least 590 V/m in free air between the electrodes and subjecting the mammal's brain region thereto.

* * * * *